(12) United States Patent
Blomme et al.

(10) Patent No.: US 11,439,746 B2
(45) Date of Patent: Sep. 13, 2022

(54) IMPLANTABLE INFUSION SYSTEM

(71) Applicant: IPADIC B.V., Deventer (NL)

(72) Inventors: Adri Marinus Blomme, Wapenveld (NL); Jozef Augustinus Elisabeth Spaan, Almere (NL)

(73) Assignee: IPADIC B.V., Deventer (NL)

( * ) Notice: Subject to any disclaimer, the term of this patent is extended or adjusted under 35 U.S.C. 154(b) by 0 days.

(21) Appl. No.: 15/736,353

(22) PCT Filed: Jun. 17, 2016

(86) PCT No.: PCT/EP2016/064057
§ 371 (c)(1),
(2) Date: Apr. 26, 2018

(87) PCT Pub. No.: WO2016/203003
PCT Pub. Date: Dec. 22, 2016

(65) Prior Publication Data
US 2018/0154074 A1 Jun. 7, 2018

(51) Int. Cl.
*A61M 5/142* (2006.01)
*A61M 5/14* (2006.01)
*A61M 5/145* (2006.01)
*A61M 39/02* (2006.01)

(52) U.S. Cl.
CPC ...... *A61M 5/14276* (2013.01); *A61M 5/1413* (2013.01); *A61M 2005/14513* (2013.01); *A61M 2039/0238* (2013.01); *A61M 2205/3337* (2013.01); *A61M 2205/3507* (2013.01); *A61M 2205/3538* (2013.01); *A61M 2205/52* (2013.01); *A61M 2205/8206* (2013.01); *A61M 2210/1017* (2013.01); *A61M 2230/201* (2013.01)

(58) Field of Classification Search
CPC ............ A61M 5/14276; A61M 5/1413; A61M 2205/3507
See application file for complete search history.

(56) References Cited

U.S. PATENT DOCUMENTS 3,527,220 A 9/1970 Summers
3,692,027 A 9/1972 Ellinwood, Jr.
3,923,060 A 12/1975 Ellinwood, Jr.
4,588,394 A 5/1986 Schulte et al.
(Continued)

FOREIGN PATENT DOCUMENTS

EP 0140727 A1 5/1985

OTHER PUBLICATIONS

Priority Search Report for NL2015004 dated Feb. 10, 2016.
(Continued)

*Primary Examiner* — Bradley J Osinski
(74) *Attorney, Agent, or Firm* — David P. Owen

(57) ABSTRACT

A system to be implanted in a living body for supplying medical substance, such as insulin. The system has a first module (1) having an inlet port (5) for receiving a transcutaneous injection of the medical substance, a second module (2) having a reservoir for storing the medical substance; a first tube (3) allowing the medical substance to flow between the first module and the second module; and a catheter (4) for releasing the stored medical substance into the living body. The first tube (3) allows the first module and second module to be implanted at different locations in the living body.

22 Claims, 8 Drawing Sheets

(56) References Cited

U.S. PATENT DOCUMENTS

| | | | | |
|---|---|---|---|---|
| 4,596,575 | A * | 6/1986 | Rosenberg | A61M 5/14276 128/DIG. 12 |
| 4,747,832 | A | 5/1988 | Buffei | |
| 5,152,753 | A * | 10/1992 | Laguette | A61M 5/1428 604/153 |
| 5,167,633 | A * | 12/1992 | Mann | A61M 5/14276 |
| 5,707,361 | A | 1/1998 | Slettenmark | |
| 6,409,698 | B1 | 6/2002 | Robinson et al. | |
| 6,764,472 | B1 * | 7/2004 | Burke | A61M 5/14276 604/288.04 |
| 7,066,915 | B2 * | 6/2006 | Olsen | A61M 5/14276 604/288.04 |
| 2002/0193751 | A1 * | 12/2002 | Theeuwes | A61M 5/14276 604/248 |
| 2013/0116667 | A1 * | 5/2013 | Ricotti | A61M 5/14276 604/891.1 |

OTHER PUBLICATIONS

International Search Report for PCT/EP2016/064057 dated Dec. 14, 2016.
International Preliminary Report on Patentability for PCT/EP2016/064057 dated Dec. 19, 2017.

* cited by examiner

IMPLANTABLE INFUSION SYSTEM

CROSS REFERENCE TO RELATED APPLICATIONS

This application is a 371 national phase of PCT application number PCT/EP2016/064057 filed on 17 Jun. 2016, which claims priority from NL application number 2015004 filed on 19 Jun. 2015. Both applications are hereby incorporated by reference in their entireties.

TECHNICAL FIELD

The invention generally relates to an infusion system which is implantable in the body. The system can be used in any (intraperitoneal) infusion therapy, in particular an insulin infusion system for a subgroup of diabetic treatments.

BACKGROUND OF THE INVENTION

For a subgroup of diabetes patients, subcutaneous deployment of insulin is not effective for a number of reasons, making it difficult for these patients to achieve a stable glucose control. Continuous intraperitoneal insulin infusion using an implantable insulin infusion system has been shown to be an effective alternative treatment mode. Intraperitoneal infusion is typically concerned with introducing a substance through the peritoneum, e.g. into the abdomen (body cavity). The benefits of this treatment emanate from more reproducible and preferential portal absorption and hepatic extraction of insulin, thereby leading to improved mimicking of the physiological situation compared with subcutaneous insulin infusion. However, the implantation of systems causes a considerable burden to the patients.

Implantable infusion systems in the prior art comprise a single housing that is to be arranged in an subcutaneous abdominal area under a fat layer and above the upper fascia of the musculus rectus abdominis, and a catheter extending into the abdominal cavity for releasing insulin into the body. The housing typically has a cylindrical symmetric shape. Such a housing requires a large space and hinders daily activities of the patient. Further, the housing contains a pump with a stroke volume of about 0.5 microL, a container for holding insulin and a refill port.

The existing infusion systems requires a surgical procedure for implantation that demands a hospital stay. The stable position of the infusion system is only obtained after encapsulation by connective tissue through time, which can take up to 6 months.

For existing infusion systems, refilling and/or rinsing of the implantable infusion system needs to be carried out by professionals (e.g. technicians/doctors) with specific tools. Locating and accessing the inlet port(s) is a difficult and tedious job for both patient and professional.

The rinsing procedure needs filling and emptying the container with fluid and forcing fluid through the housing, the fluid being saline to remove remains of old insulin or soda to remove insulin crystals before refilling.

Existing implantable infusion systems typically comprise a battery in the housing (thus inside the body) for operating the infusion system. The life time of the battery is claimed to be 6 years but the life time of the device is typically shorter due to complication or failure of either catheter or electronics. Any failure of the system requires a complete new surgical procedure as if it were a new system placement, and requires general anesthesia, i.e. a medically induced coma and loss of protective reflexes for the surgery, resulting from the administration of one or more general anaesthetic agents.

The surgical procedure for typical implantable infusion systems can be described as follows. An incision through skin and one or more fat layers is made according a pre-indicated line. A pocket is made subcutaneously. A catheter is placed through the rectus muscle in the abdominal cavity with its tip in the direction of the liver and the catheter is fixated between peritoneum and posterior rectus sheath. Ligations to the housing are made at three points. An antibiotic mat is placed, the housing is placed and the ligations fixated. Pocket and skin are closed in two layers with absorbable sutures.

The catheter function can be affected by insulin crystallization and encapsulation or blockage at its distal outlet by protein. Such insulin crystallization and protein disposition at the distal end of the catheter considerably hinders the function of the catheter. For instance, these proteins form a layer, which makes the release rate of insulin irregular. This results in poorly or even uncontrolled insulin levels in the body. Although the catheter sometimes can be flushed with saline to remove debris in the catheter and free the catheter exit, this often requires another surgical procedure.

The reservoir in the housing typically has a dead volume space of about 3 ml which is about 20% of the maximal container volume and forms a waste of space which requires the patients to visit refill stations more frequently. It also leads to loss of expensive insulin since it has to be removed by rinsing which is per definition less effective with a large dead volume.

Due to the above-mentioned reasons, existing implantable infusion systems are still unreliable, inconvenient and/or uncomfortable for patients to use.

SUMMARY OF INVENTION

It is therefore an objective to reduce any of the above or other drawbacks of existing implantable infusion systems, e.g. reducing the burden for the patient.

A first aspect of the invention relates to a system adapted to be implanted in a living body for supplying medical substance, such as insulin, as defined in claim 1. The living body is preferably, but not limited to, the living human body.

The system according to the invention is arranged for receiving the medical substance (e.g. filling/refilling), e.g. for receiving a transcutaneous injection of the medical substance; storing the received medical substance; pumping the medical substance to a catheter, and releasing the stored medical substance from the catheter into the living body. These functions are allocated in two or more modules, including a first module for said receiving of the medical substance and a second module for at least one of said storing and pumping of the medical substance. Preferably the function of receiving the medical substance is separated from the function of storing the medical substance in different modules.

The system may comprise:
a first module, arranged in a first housing adapted to be completely placed under the skin. The first housing has an inlet port for receiving a transcutaneous injection of the medical substance; and/or
a second module, arranged in a second housing, having a reservoir for storing the medical substance; and/or
a first tube, arranged to allow the medical substance to flow between the first module and the second module; and/or a catheter for releasing the stored medical substance into the living body.

Preferably the first housing and the second housing are adapted to be placed above the peritoneum of the body, and/or preferably the second housing is adapted to be placed deeper under the skin than the first housing.

The system may comprise a first tube arranged to allow the medical substance to flow between the first module housed in a first housing and the second module housed in a second housing, which allows the first module and second module to be implanted at different locations, in particular subcutaneously and at different depths under the skin, in the living body. The housings are adapted to be fully implantable below the skin of the living body. Preferably, the first housing is adapted to be placed under one or more fat layers and above a fascia layer, such as the upper fascia of the musculus rectus abdominis, and the second housing is adapted to be placed between the musculus rectus abdominis fasciae, e.g. below the upper fascia. Relevant functions (e.g. an inlet port for receiving the medical substance, a reservoir for storing substance, and a pump/catheter for releasing substance) thus do not need to be confined in a single location within a single housing in the living body. The system of the invention thus has an advantage that the spatial arrangement of the system (e.g. location, size) can have greater flexibility and be adapted to the respective function(s), and shapes of system elements may be further adapted to the respective locations of implantation. For example, the function of receiving the medical substance (e.g. refilling using a refilling device) and the function of storing the medical substance can be separated. This achieves the objective to reduce the burden of the patients.

The first module may have an inlet port for receiving the medical substance, such as insulin. The inlet port can form an exterior part of the first housing. The inlet port and the first housing are preferably arranged to be implanted subcutaneously. The inlet port is preferably a transcutaneous inlet port, which in use is located under the skin of the living body. In use the inlet port is closed and the inlet port can be reached e.g. using a needle/syringe. The needle/syringe can be used to subcutaneously inject a medical substance by penetrating the inlet port, allowing the inflow of medical substance in the first module. The inlet port can be arranged to receive the subcutaneous injection of medical substance. In embodiments the inlet port is adapted to cooperate with a patient skin penetrating medical substance supply device. The supply device is arranged to penetrate the skin of the patient to reach the inlet port. This takes away the necessity of providing a connection through the skin, e.g. using a tube.

Preferably the first module is provided with/connected to a catheter for releasing the medical substance into the body. In this embodiment medical fluid is received first in the first module, is subsequently stored in the reservoir in the second module and is distributed to the body again via the first module. Means to distribute the medical substance can be part of the first module and the first module can be positioned closer to the skin of the patient. This allows quick replacement. The voluminous reservoir can be positioned deeper, lowering the discomfort for the patient. The second module is a rather passive module acting as a reservoir, whereas more active parts of the system are housing in the first module. Further, the system may comprise a power source, such as a battery, which is preferably arranged in the first module.

The second module may have a reservoir for storing the medical substance received by the first module. Further, the second module may comprise a pump. The pump is arranged to pump the medical substance from the reservoir and to deliver the medical substance to the catheter. In this embodiment, the reservoir and/or the pump are received in the second housing, the second housing arranged to be implanted subcutaneously.

The first tube may be arranged to conduct the medical substance (and/or rinsing liquid, and/or electrical signals) between the modules in a bi-directional way. Alternatively, the system may further comprise a second tube, wherein the first tube is arranged to conduct the medical substance and/or rinsing liquid from the first module to the second module, and the second tube is arranged to conduct the medical substance and/or rinsing liquid from the second module via the first module to the catheter.

The system may comprise a control circuit and a processor in the first module and/or in the second module. The control circuit and the processor are arranged to configure the pump for delivering a desired amount of medical substance from the reservoir, via the catheter to the living body. The desired amount of medical substance may be determined on the basis of a signal received from a glucose sensor.

In an embodiment, the first module comprises a controllable valve for connecting and disconnecting the inlet port via the first tube to the reservoir. In an embodiment the first module comprises a controllable valve for connecting and disconnecting the catheter via the first tube to the reservoir.

A second aspect of the invention relates to a system adapted to be implanted in a living body for supplying medical substance, such as insulin, as defined in claim 23. Any feature of the second aspect can be combined with other aspects.

The system may comprise a catheter and a housing for at least two operational elements that is to be arranged in the subcutaneous abdominal area, and an inlet port for receiving the medical substance. Preferably the entire inlet port is adapted to be placed subcutaneously, e.g. under a skin layer. The housing may incorporate the first module and/or the second module of the first aspect of the invention. The housing has a shape adapted to the anatomical location it is placed at. This shape adaptation increases the level of comfort of the patients, and reduces the burden of implantation and maintenance of the implantable pump system.

Preferably (although not indispensable), the shape of the housing lacks a cylindrical symmetry. An absence of a cylindrical symmetry has an advantage of restricting rotation of the housing in the body and enhances the bodily reactions in fixating its position.

A third aspect of the invention relates to a catheter for an intraperitoneal release of a medical substance, such as insulin, as defined in claim 29, and a system comprising the catheter, as defined in claim 33.

The catheter comprises means for disturbing formation of a protein layer and/or crystallization of the medical substance, at the distal end of the catheter. The catheter may have an inner core and outer tube, which have relative movement to each other from time to time for disrupting crystallization of the medical substance and encapsulation by protein at the distal end of the catheter. The relative motion can either be translational or rotational. The catheter function is thus no longer affected by insulin crystallization and protein encapsulation.

A fourth aspect of the invention relates to a kit of parts, the parts formed by modules, for putting together for forming or that can be assembled to form a system according to any of the first, second, and third aspects of the invention, as defined in claim 35. Example modules of the kit of parts are:

housing parts, battery, reservoir, pump, tubes, inlet port, controller, wireless receiver/transmitter/transceiver, etc.

The kit may comprise a plurality of modules. One or more modules can form and/or are received in a first housing for receiving the medical substance and for releasing the medical substance into the body; and a catheter, to be connected to the first housing, for releasing the stored medical substance into the living body. The plurality of modules may comprise two or more interchangeable inlet modules for adapting a length of an extending portion of the first housing.

The modules are combined to form the first housing, which preferably comprises a body and an extending portion. The extending portion preferably has a length adapted to a thickness of one or more fat layers, so that the housing can have a portion, e.g. the inlet port for a fluid, preferably a transcutaneous inlet port, e.g. having a surface that can be penetrated by a syringe, just under the skin to receive a needle. Adaptation of the length of the extending portion will make it easier to reach the subcutaneous portion. The variable length allows overcoming differences, e.g. thickness of fat layers, between patients.

The adaptable length of the extending portion may be achieved by using a plurality of adapters as the interchangeable inlet modules, each having a different pre-determined length for adapting a portion that receives the needle and the body that is implanted under fat layers. In another embodiment, each interchangeable inlet module may have an integrated extending portion and an inlet for receiving the needle. A kit of parts or modules may comprise a plurality of such integrated inlet and extending portion, to be selected to achieve different lengths. In yet another embodiment, the entire first housing may form as an integral unit. In this embodiment, the interchangeable inlet modules are thus different types of the first housing with a different size. The doctor may thus choose between different types of the first housing with different lengths of the inlet port.

Each aspect of the invention may have one or more of the features as described below.

In an embodiment, the first and second modules, the first tube and the catheter are preferably arranged to be implanted subcutaneous. The catheter is preferably connected to the first module. In an embodiment, the first tube is arranged to conduct the medical substance from and to the first module and the second module.

In an embodiment, the first module comprises: a first liquid connection connecting the first tube to the catheter; a second liquid connection connecting the inlet port to the first tube. The first liquid connection may be arranged to allow the stored medical substance to be pumped via the first tube to the catheter and released to the living body via the catheter. The second liquid connection may be arranged to allow filling and/or refilling of the system. Preferably, the first and second connections are formed by a controllable valve. The first module may further comprise a third liquid connection between the inlet port and the catheter. The third liquid connection may be arranged to allow rinsing of the catheter. The three liquid connections may be formed by one or more controllable valves. Preferably all three liquid connections are formed by a single controllable valve, e.g. a multivalve.

In an embodiment, the system, preferably the first module, is provided with a power supply, such as a battery, for supplying an electronic power to the system, preferably to both the first module and the second module.

By arranging one or more maintenance sensitive elements in the first module to control the second module, the latter can be placed deeper. In this way, the deeper location of the second module does not hinder maintenance of the system, because the one or more maintenance sensitive elements are arranged in the first module, which can be arranged just under the skin, e.g. the inlet port having a length adapted to the thickness of fat layer(s).

In an embodiment, the system, preferably the first module, is provided with a rechargeable battery, and a charging circuit for receiving a contactless charging signal from a charging device, wherein preferably the charging circuit is provided in or close to the inlet port.

The system may further comprise a charging device for emitting a charging signal for the charging circuit.

Contactless charging typically needs a short distance between a charging device and a receiving charging circuit. Such a short distance is made possible by the invention. The charging circuit is preferably arranged in the first module, preferably in the extending portion and/or in close proximity to the inlet port. In this way the distance between the charging circuit and the surface of the skin is short enough to carry out contactless charging. In an embodiment, the charging circuit is arranged on a portion of the first housing that is adapted to be towered toward the skin, for example a top face of the inlet port having a length adapted to the thickness of fat layer. As such, the top face is placed just under the skin, and the contactless charging becomes possible.

In an embodiment, the first tube provides an electrical connection between the first module to the second module.

In this way, the first module and the second module can be electrically connected to each other via the first tube. By integrating the function of conducting liquid and the function of conducting electrical currents, it is no longer needed to arrange an extra electrical wiring. The overall connection between modules can therefore be kept simple.

In an embodiment, the system, preferably the second module, comprises a pump for pumping the medical substance from and/or to the reservoir. The second housing is arranged to be positioned subcutaneously at a larger distance from the skin than the first housing, thereby positioning the reservoir 'deeper', which results in less burden for the patient and/or more available space in the patient.

The system may further comprise a glucose sensor for measuring a value representing a level of blood sugar, wherein the system is arranged to control pumping and or releasing of the medical substance via the catheter in response to the measured value.

In an embodiment, a second housing of the second module has a closed-off an internal volume that receives the reservoir. A shape of the reservoir may be arranged to change, in dependence of an accumulated release of the medical substance. Preferably the internal volume further is filled with a material adapted to transform between a liquid phase and a gas phase in in dependence of the internal volume.

In this way, when the amount stored medical substance decreases, the volume of the reservoir can be reduced. The shape of reservoir and it containment in the housing of module reduces the minimal allowable volume of the reservoir and hence its dead volume. As a result, the frequency for refilling can be reduced, and the waste of the medical substance in the dead volume can be kept in minimum.

In an embodiment, the first module is arranged in a first housing, wherein the inlet port comprises a self-sealing material, preferably comprising rubber. The inlet port is arranged as a transcutaneous inlet port, the self sealing material forming part of a surface of the exterior of the first housing.

In an embodiment, the inlet port is preferably one or more of: —dome-shaped; —positioned on a generally flat side of the first housing; and/or —shaped to extend from the first housing. The inlet port (5) preferably towers from the first housing in a range between 1 cm and 4 cm, preferably between 0.5 cm and 8 cm.

The abdominal wall typically has a plurality of skin layers on the top. Under the skin layers are one ore more fat layers. Under the fat layers are a plurality of musculus rectus abdominis fasciae. The thickness of the fat layers depends on whether the patient is thin or fat.

The inlet port towers from the first housing with a variable length forming an extending portion thereof. A variable length of the inlet port has an advantage that the length can be adapted to the thickness of one or more fat layers, such that the inlet port extends from a surface of the first housing through one or more fat layers to reach a location in a close proximity to a skin layer, e.g. less than 1.5 cm, preferably less than 1 cm, more preferably less than 0.5 cm, under a lowest skin layer, regardless of whether the patient is fat or thin. This can simplify processes of refilling and/or charging, e.g. making it easier to locate the inlet port.

The variable length may be achieved by providing a plurality of interchangeable inlet ports having different pre-determined lengths. When implanting the system, one of the inlet ports with a suitable length can be selected in accordance with the thickness of the one or more fat layers.

The first housing, which can include the inlet port, is preferably adapted to be placed subcutaneously, e.g. mounted on a top layer of fasciae (e.g. the upper fascia of the musculus rectus abdominis). In an embodiment, the first housing comprises a plate-like body, wherein the inlet port extends from the plate-like body to the skin. Thanks to the separation of the receiving function and the storing function, the first module does not need to be subject to the capacity of the reservoir. The plate-like body of the first module can be made smaller, e.g. the plate-like body may have a thickness less than 2 cm, preferably less than 1 cm.

In an embodiment, the first module comprises a control circuit for controlling the second module to pump the stored medical substance to the catheter to release the medical substance into the living body, preferably comprising a memory that can contain instructions for configuring the pumping and/or releasing of medical substance.

In an embodiment, the catheter is connected to the first module, wherein the first module comprises three operation modes, wherein:

in a first mode, the first module is configured to allow the medical substance to flow from the first tube to the catheter;

in a second mode, the first module is configured to allow the medical substance to flow from the inlet port to the first tube; and in a third mode, the first module is configured to allow fluid to flow from the inlet port to the catheter for rinsing the catheter.

By connecting the catheter to the first module, three directions of liquid flow can be controlled using a single switch, e.g. a multi-directional valve.

In an embodiment, the first module is adapted to be positioned subcutaneous and the second module is adapted to be positioned deeper than the first module in the living body.

In an embodiment, the second module is arranged in a second housing, wherein the first tube has a length between 4 cm and 15 cm, more preferably between 6 cm and 12 cm, for allowing the second housing to be placed in a space between musculus rectus abdominis fasciae.

The separation of the first and second modules allows elements that might need to be repaired/replaced (e.g. electronic circuit, batteries, switches, etc.) to be arranged in the first module that is arranged more superficially. The second module can therefore be placed under a deeper subcutaneous layer than known systems. Arranging the second housing in the space between musculus rectus abdominis fasciae can provide a much better fixation than known systems, which place the single housing in fat layers. In this way, the level of comfort can be increased, and the burden of the patient can further be reduced.

In an embodiment, the first module is arranged in a first housing, the second module is arranged in a second housing, and at least one of the first housing and second housing have a plate-like shape, preferably having one or more rounded edges, preferably, the plate-like shape comprises a plurality of faces each having a generally quadrilateral shape. A face is a surface area defined by one or more edges. The plate-like shape may form a quadrilaterally-faced hexahedron having one or more curved edges, wherein a distance between two unconnected faces of the hexahedron is less than ⅓ of a square-root of the area of one of the two unconnected faces. Preferably, at least two unconnected faces of the housing are elongated. For example, the second housing may form a cuboid having a length, a width, and a thickness. The thickness is smaller than the length and the width. The cuboid shape preferably has one or more curved edges along a direction of length and/or a direction of width. Other edges, e.g. edges along the direction of thickness, may be substantially straight or may also be curved. The plate-like shape (e.g. plate-like cuboid) may have a general bar shape, preferably a wind shield shape, preferably having a top face and a bottom face and preferably four side faces. The top face and the bottom face are preferably connected. The top face and the bottom face may be connected to the side faces over two curved edges and over two generally straight edges, wherein preferably the top face and/or the bottom face are curved in a direction perpendicular to the straight edges thereof, the top face and the bottom face preferably having a different curvature. An embodiment is shown in FIG. 2.

A shape lacking a cylindrical symmetry is found effective to restrict rotation and displacement of the housing in the living body, thus providing a better fixation and increasing the level of comfort.

In an embodiment, the first module comprises a magnet or an electromagnetic coil, preferably in or close to the inlet port, to be attracted by an electromagnetic force generated outside the living human body. The term 'electromagnetic' refers to any interactions between electrically charged particles, also including electrostatic forces and magneto-static forces.

The system may further comprise a locator device for locating the first module by an electromagnetic force.

By providing a magnet or an electromagnetic coil, the first module under the skin can be easily located by an (electro) magnetic device. In this way, the process of refilling/rinsing/charging can be simplified.

In an embodiment, the housing for storing the medical substance has a plate-like shape having a top face and a bottom face, the top face and the bottom face defining a thickness of the plate-like shape. The top face may have a first curvature, and the bottom face has a second curvature, the first curvature and the second curvature are such that the plate-like shape has a non-uniform thickness. The housing preferably has one or more rounded edges, preferably having a generally rectangular shape. Preferably, the housing has a general bar shape, preferably a wind-shield shape, the housing comprising:

a top face;
a bottom face; and
a plurality of side faces, preferably four side faces, The top face and the bottom face are preferably connected to the side faces over at least two curved edges and over at least two generally straight edges. Preferably, the two curved edges have a different curvature.

In an embodiment, the housing for storing the medical substance has a non-uniform thickness, e.g. a distance between the top face and the bottom face defines the thickness of the plate-like shape. The housing preferably has a gradual change of thickness along an edge of the housing.

A non-uniform thickness is found effective to restrict the displacement or dislocating of the housing in the body. It can also minimize abrupt changes in the thickness, so the tissue can better form around it. It also allows the reservoir to be shaped in a way that its dead volume (minimal volume) is reduced and volume variations between minimal and maximal volumes are optimized.

The catheter may have an inner core extending through a portion or a complete length of an outer tube. The inner core of the catheter may have a shape without a hollow space or have a shape of a tube comprising a hollow and one or two openings. The portion may form a part or form a complete length of the outer tube. The inner core preferably extends from the outer tube at the distal end. The relative movement may be in an axial direction, rotational direction or a combination of the two. It is proven that such a relative movement can effectively disturb a formation of a protein layer around the distal end of the catheter. As the inner core and the outer tube have the relative movement from time to time, the formation of the protein layer is disturbed and can no longer hinder the release of the medical substance. It also reduces the possibility of crystallization of solutes.

In an embodiment, the distal end of the inner core (e.g. a tip extending from the outer tube at the distal end) has a diverging diameter, preferably at most a diameter corresponding to the outer diameter of the outer tube.

In an embodiment, the catheter is arranged to allow a flow of the medical substance along a space between a side-wall of the inner core and an inner side-wall of the outer tube.

In this way, substantially all the way through the path of the flow of the medical substance can benefit from the relative movement. Thus, not only around the tip, but also along the sidewall of the catheter, the formation of the protein layer and crystallization of the medical substance can both be restricted.

In an embodiment, the catheter is arranged to allow a flow of the medical substance along a hollow in the inner core, wherein the inner core comprises one or more openings for releasing the medical substance from the hollow to the gap. The inner core may be in the form of an inner tube. Preferably, openings in the inner tube to the hollow space are arranged proximal from the diverging diameter part. In an embodiment, the part of the inner tube with diverging diameter forms a circumferential opening or gap with the outer tube for releasing medical substance at the tip from the catheter.

In an embodiment, the inner core comprises a first portion at the distal end, having a larger radius, and a second portion having a smaller radius.

The larger radius and the smaller radius result in a non-uniform cross-section area along the flow of the medical substance. This is found effective to disturb a laminar flow of the liquid around the distal end. In The different radiuses of the first portion and the second portion can disturb the liquid that contains protein. This can increase the effect of the relative movement to disturb the formation of the protein layer.

The system (e.g. the first module) can also house a battery and communication units. The housing for storing the medical substance may contain parts that are highly reliable and does not need servicing over its expected life time which may be up to 10 years.

Any feature disclosed herein, part of any of the disclosed aspects, can be combined to form an embodiment according to this disclosure.

BRIEF DESCRIPTION OF DRAWINGS

Embodiments will now be described, by way of example only, with reference to the accompanying schematic drawings in which corresponding reference numbers indicate the same or corresponding elements, and in which.

The figures are meant for illustrative purposes only, and do not serve as restriction of the scope or the protection as laid down by the claims. Any of the features disclosed in the figures and/or in the description can be taken in isolation unless explicitly indicated that it cannot. Any feature in the figures and description having an explicit or implicit advantage can be the basis for a divisional application.

DESCRIPTION OF EMBODIMENTS

Figure 1:
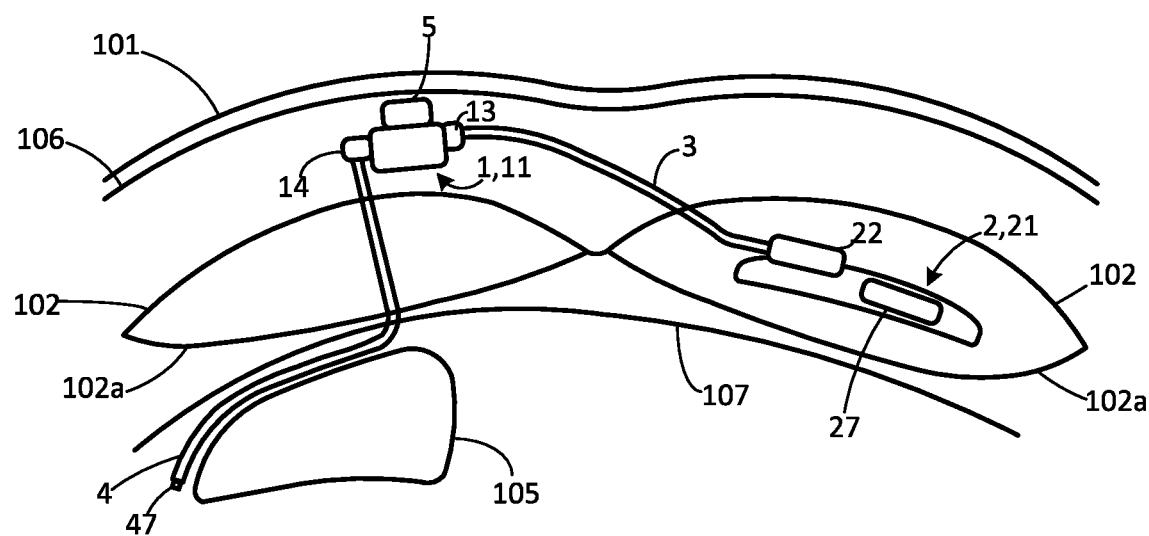
FIG. 1 schematically shows a cross-section view of an embodiment of the system of the invention.

FIG. 1 schematically shows an embodiment of a system according to the invention. The system is adapted to be implanted in a living body for supplying medical substance, such as insulin, into the living body, e.g. for infusion treatments. A preferred medical substance is insulin. All the terms 'medical substance' described below may comprise any kind of insulin.

The system according to a first embodiment shown in FIG. 1 comprises a first module 1, a second module 2, a first tube 3 connecting the first and second modules, and a catheter 4 adapted to extend into the abdomen cavity for releasing the medical substance. The system is adapted to be implanted below the skin 101 of a living body.

The system has functions of at least: (1) receiving the medical substance; (2) storing the received medical substance; and (3) releasing the stored medical substance into the living body. According to the system of the invention, these functions are allocated in two or more different modules, arranged in two or more different housings. In the embodiment shown, the first module 1 is arranged in a first housing, and the second module 2 is arranged in a second housing.

The first module 1 is arranged for receiving the medical substance transcutaneously. In the embodiment shown, the first module 1 comprises an inlet port 5 for receiving a transcutaneous injection of the medical substance.

The second module 2 is arranged for storing the received medical substance. For example, the second module 2 may comprise a reservoir 27 for receiving the medical substance via the first tube 3. In the embodiment shown, the second module is arranged in a second housing 21, which is separate from the first housing.

The catheter 4 is arranged for releasing the stored medical substance into the abdomen cavity, preferably at a location close to the liver 105. The catheter 4 may enter the abdomen cavity, and may have a distal portion or tip extending in a direction having a tangent substantially parallel to a surface of the liver.

The distal end of the catheter may comprise a fixation element, e.g. in the form of a protruding part at the distal end of the catheter, arranged to be grabbed during laparoscopic procedures and/or that can be used for fixation in the living body.

The first module 1 and the second module 2 are adapted to be placed at different locations in the living body, as shown in FIG. 1.

In this way, the receiving, storing and pumping functions of the system do not need to be confined in a single location anymore. The spatial arrangement of the system (e.g. location, size) can have a greater flexibility and be adapted to the respective function(s), and shapes of system elements may be further adapted to the respective locations of implantation.

By dividing functional elements into two or more physical separated housings, the size of each housing can also be reduced and optimized such that the sum of volumes is smaller than a pump system realized in a single unit as is presently the case. Moreover, each part can have a shape adapted to a corresponding function and/or the location in the body. In this way, the shape and reduced volume of the modules will make the patient feel better in the daily life experience.

A typical anatomy structure of the abdominal wall is shown in FIG. 1, the abdominal wall has a plurality of skin layers 101 on the top. Under the skin layers 101, there are one ore more fat layers 106. Under the fat layers 106, there is a plurality of musculus rectus abdominis fasciae, including an upper fascia 102 and a lower fascia 102a. The lowest layer, which defines the boundary of the abdominal wall and the abdomen cavity, is the peritoneum 107.

The housing of the first module is preferably adapted to be placed under one or more fat layers, preferably mounted on the upper fascia 102 of the musculus rectus abdominis, under fat layers. The housing of the second module 2 is adapted to be placed deeper than the first module, preferably in a space between the musculus rectus abdominis fasciae 102a, 102b.

In this way, a good balance between fixation in the body and control/maintenance of the system can be achieved. Thanks to the division of functions, the second module 2 can be specifically adapted to the function of storing the medical substance and housing low-maintenance units of the system, and can be adapted to be placed in a deeper location than known systems. As such, a better and immediate fixation of the second module 2 can be achieved. The deeper location of the second module 2 does not hinder maintenance of the system, because sensitive parts can be arranged in the first module 1, which is arranged just under the skin 101, and consequently surgical maintenance of the first module 1 only needs local anesthesia and therefore can be done in day care.

Figure 1A:
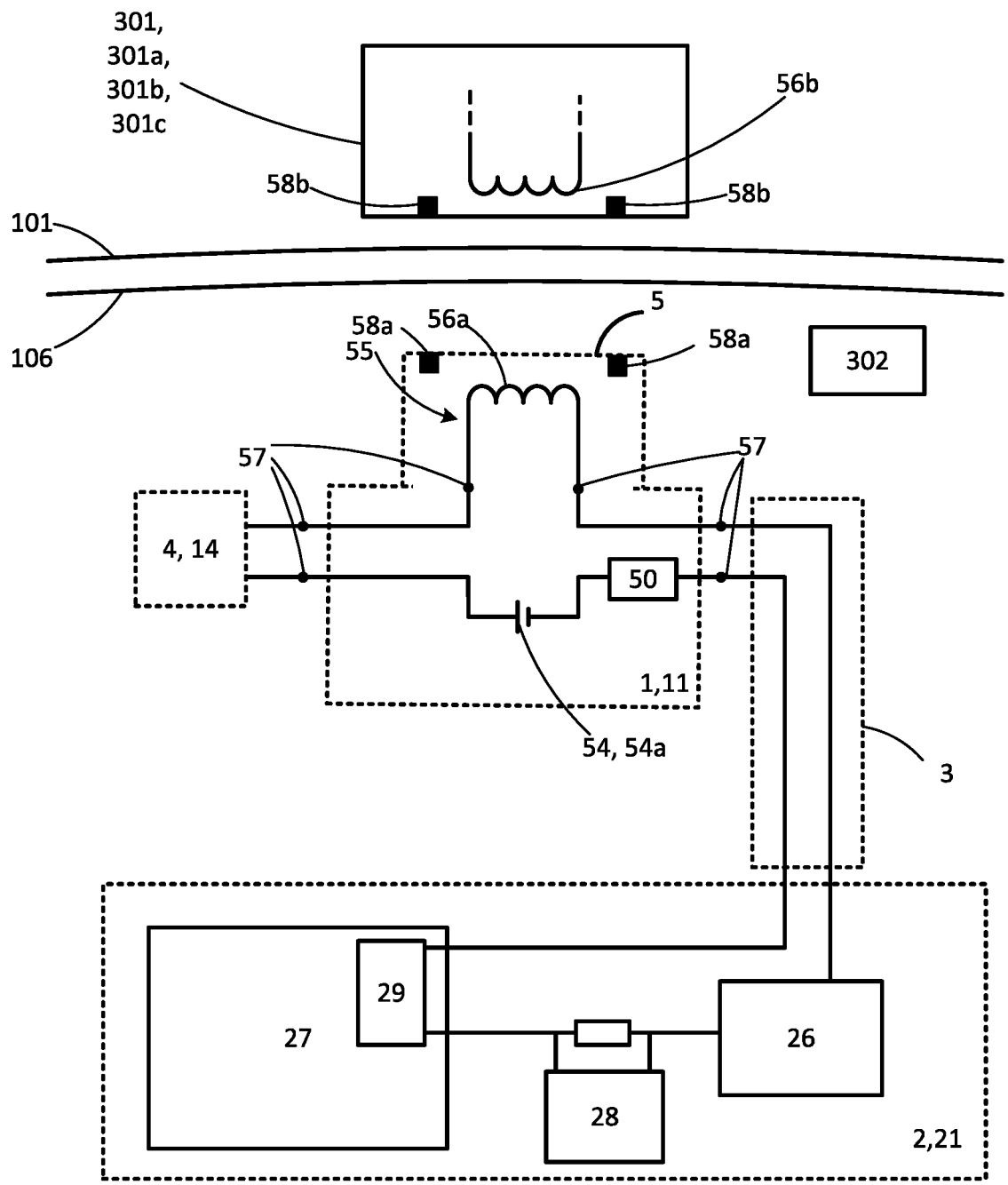
FIG. 1A shows an embodiment of electrical connections between different modules of the system.

For example, as shown in FIG. 1A, the first module (in particular the inlet port 5) may comprise a control circuit 50 for communicating with a control device 301a outside the body for operating or charging the system. As the first module 1 is closer to the skin, communication is easier. Communication can be bi-directional. Instructions, such as dose settings, can be provided to the control circuit 50. Also log data may be stored in a memory. The memory may be connected to the control circuit 50. The log data may include a historical data related to the release/pumping of the medical substance. The memory may comprise setting or configuration data of the system. The control circuit 50 may be arranged to send the setting or configuration data to an external device for technical maintenance or a check by professionals.

Additionally or alternatively, the system, preferably the first module, may comprise a power supply 54, which may comprise a rechargeable battery 54a. The first module 1 may comprise a charging circuit 55 comprising a first induction coil 56a for receiving to an alternating electromagnetic field from a second induction coil 56b, arranged in an external (portable) charging device 301b. The first induction coil (in the first module 1) can then convert the electromagnetic field back into electrical current to charge the battery.

In the embodiment shown, the external control device 301a and the charging device 301b are integrated. Alternatively, the control device and the charging device may be separate devices.

Contactless charging typically needs a short distance between the first induction coil and the second induction coil. In the system of the invention, such a requirement of a short distance is not a problem. As the first module 1 is adapted to be placed just under the skin 101, the patient only needs to keep a charging device above the skin to achieve the needed short distance. This can be further facilitated by a magnetic positioning device 301c, which may be integrated with the control device and/or the charging device. The first module 1 may comprise one or more magnetic elements 58a to be attracted by the magnetic positioning device 301c. The first module 1 thus makes it possible to utilize contactless charging of the rechargeable battery during convenient time intervals.

In the embodiment shown, the magnetic element 58a is arranged on the inlet port in order to be close to the skin 101. In other embodiments the one or more magnetic elements 58a are arranged on a plate-like body of the first housing 11.

In this way, the battery volume and weight of the overall system, especially the first module 1, can be reduced since it needs only charge for a limited amount of time. The limitation of the lifetime of the battery can now be determined by the cycles of charging and discharging, thus well extend over more than 6 years, thus longer than known systems. Battery failure can be corrected by replacing the first module 1 with minimal surgery under local anesthesia.

Consequently, the system provided with such a charging circuit further increases the convenience and the comfort of the patient, while further reducing costs for health care.

The first tube 3 may be arranged for transporting the medical substance as well as conducting electrical signals and/or an electrical current. The side wall of the first tube 3 may comprise a multi-layer thin-film structure, provided with two or more conductive layers. Alternatively, wiring may be incorporated in the wall.

The system may comprise a pump 26 for pumping the medical substance into the abdominal cavity. In an embodiment as shown in FIG. 1, the pump 26 is arranged in the second module 2, but may in other embodiments be arranged in the first module 1. The role of the pump is to pump the medical substance from the reservoir 27 into the first tube 3 by which it is guided into the first module 1 from where it is guided into intraperitoneal space by the catheter 4. The pump is electrically connected to the electronic circuit controlling its action.

The pump 26 may be steered by electronic circuitry depending on insulin demand determined at about 4-5 time points a day by a standard home glucose test instrument or continuously. A processor connected to a memory is programmed in accordance with instructions from a doctor to release the medical substance. In an embodiment the instructions can be amended using a wireless connection. The processor may be arranged in/provided with the control circuit 50 in the first module 1. Alternatively or additionally, the system may comprise a processor 28 in the second module 2.

The system may comprises a glucose sensor 302 for determining the blood sugar level. The glucose sensor may be adapted to be placed subcutaneously, adapted to be implanted, or adapted to be placed percutaneously. The glucose sensor is preferably arranged to communicate (wired or wirelessly) with the first module 1. With a continuous sensor the communication may be continuous as well or intermittent at a predetermined frequency suitable for controlling the pump. In case glucose levels are measured manually with a glucose meter, the meter preferably comprises means for transmitting a measured value representing the blood sugar level wirelessly to the first module 1 (directly or indirectly via an external communication device). The first module 1 may be arranged to transmit a command to the second module 2 for operating the pump.

The reservoir in the second module 2 is arranged for accommodating the received medical substance. The reservoir may have a variable volume. The variable volume may be configured to at least a first (smaller) value and a second (larger) value. The second module 2 may be arranged to change a shape of the reservoir for changing the volume of the reservoir.

The variable volume may depend on an accumulated amount of release of the medical substance. The variable volume has two extremes: a first (lowest) volume and a second (highest) volume. For example, the reservoir 27 may be formed of a flexible material (e.g. synthetic material or deformable metal structure). The reservoir 27 may be arranged to close off liquid and gas. In this way, the volume of the reservoir decreases with the amount of medical substance stored in the reservoir 27, and in this way the reservoir 27 can become a low-maintenance element which does not needs electrical power or wiring. Alternatively or additionally, the second module 2 may comprise a device 29 to assert a force on the flexible material for changing the shape of the reservoir 27 and/or to measure the volume of the reservoir. The device 29 may be arranged in/on/closed to the reservoir, and may be electrically connected to the power supply of the system. The first volume may determine the dead volume of the system and can be minimized by compressing the flexible material. In the second state, the reservoir may fill the second housing 21 to a higher degree, e.g. at least 80% of a total volume of the second housing 21.

In this way, dead volume of the reservoir can be reduced. This contributes to a reduction of frequency for refill, and the waste of the medical substance in the dead volume can be kept in minimum. On the other hand, the overall volume of the housing 21 of the second module 2 may also be reduced. Either way, the overall level of comfort is improved.

The internal volume left between the second housing 21 and the reservoir may be closed off by the second housing 21, such that exchange of gas and liquid with the surrounding space in the living body is restricted. In operation of the system, the space may be filled with a material which changes between a liquid phase and a gas phase in response to the volume change of the reservoir. For example, when the reservoir expands and the internal volume is reduced, the material changes from the gas phase to the liquid phase. On the other hand, when the reservoir is compressed and the internal volume is increased, the material changes from the liquid phase to the gas phase. A suitable material is Freon. In this way, the reservoir may change volume without/with minimal change of pressure in the housing, so as to maintain a pressure substantially independent of filling of the volume/state of the reservoir.

Apart of the primary functions of these modules they also may contain other parts of the infusion systems, such control units, memories, or electronic circuits.

Figure 1B:
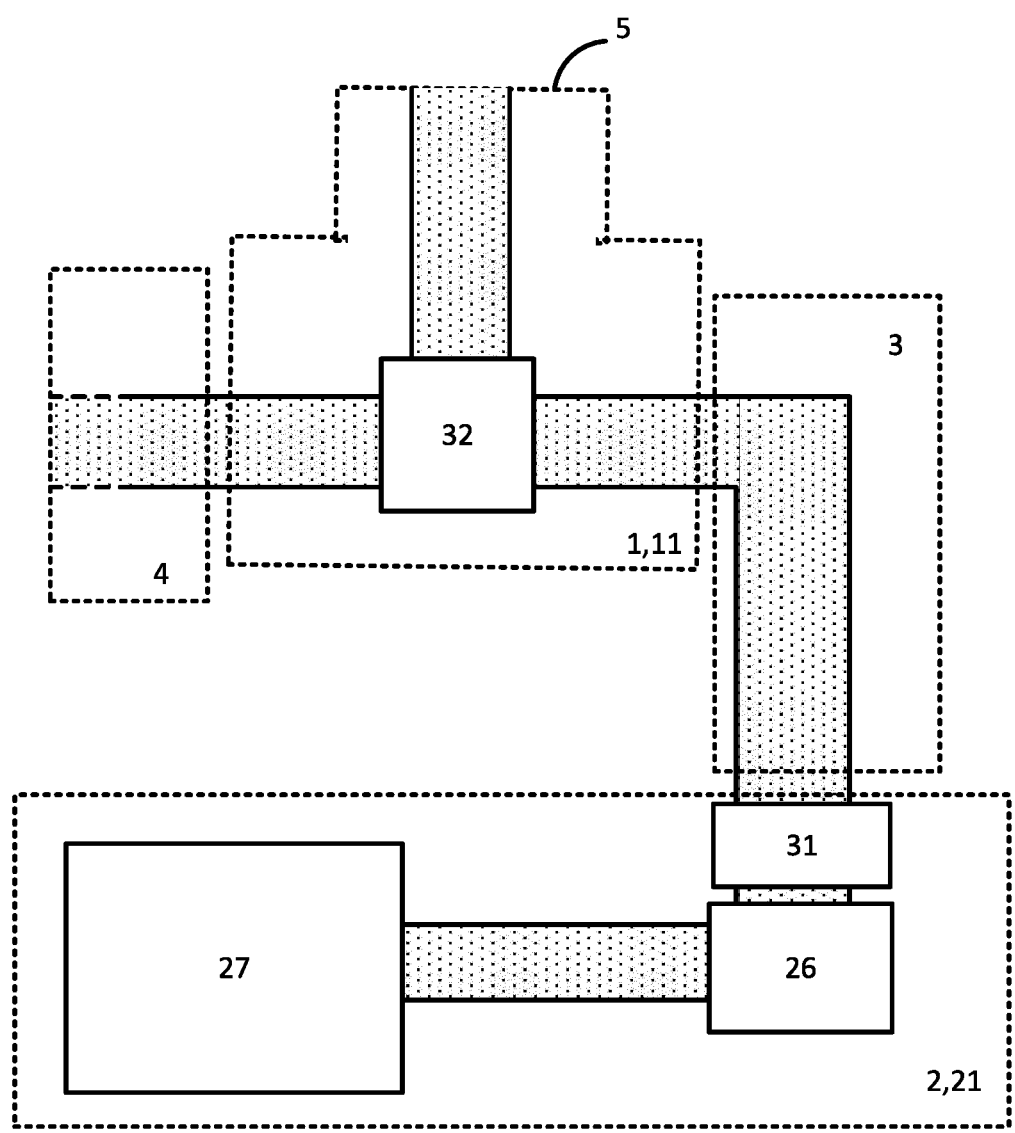
FIG. 1B shows an embodiment of liquid connections between modules of the system.

FIG. 1B shows an embodiment of the system according to the invention, which conceptually shows a flow of the medical substance between different modules of the system.

The system may comprise a first valve 31 (e.g. a multi-directional valve), shown as a functional box. The first valve 31 is received in one of the housings, preferably in the second housing 21. When set in a first position, the first valve 31 allows liquid to flow from the reservoir 27 to the first tube 3 from the pump 26. When set in a second position, the first valve allows liquid to flow from the first tube 3 to the reservoir 27. The second position can thus be used for (re)filling of the reservoir and rinsing. The position of the first valve can be set either by following the pressure increase at filling or pressure decrease at fluid withdrawal as with rinsing. The function of the first valve may be controlled electronically.

In a preferred embodiment, the first valve 31 and the pump 26 are both arranged in the second module 2, as shown in FIG. 1B.

The first module 1 may contain one or more second valve(s) 32, shown as a functional box, for allowing three different modes of operation. In a first mode, the standard mode, it allows exclusive fluid flow from the tube 3 directly into the catheter 4 supplying medical substance to the intraperitoneal space. In a second mode, it allows exclusive fluid flow from the inlet port 5 to the tube 3 allowing filling of the reservoir by medical substance or rinsing the reservoir and pump by a rinsing solution, such as Saline or Soda. In a third mode, the valve allows fluid flow from the inlet port to the catheter 4 for rinsing the catheter or the use of an external pump in case of an emergency.

In this way, switching between operation and refilling of the system can be controlled by the first module 1, which is adapted to be placed just under the skin. A mechanism for rinsing can also easily be added using the same tube(s), without substantially making the electrical/physical connection more complicated.

The first tube 3 may be arranged to conduct the medical substance and/or rinsing liquid between the modules in a bi-directional way. Alternatively, the system may further comprise a second tube (not shown) connected between the second housing 21 and the first housing, wherein the first tube is arranged to conduct the medical substance and/or rinsing liquid from the first module to the second module, and the second tube is arranged to conduct the medical substance and/or rinsing liquid from the second module to the first module.

The above mentioned different functions may be switched by activation of multi positional valves controlled by an external electronic signal transmitted from the internal electronic circuit in the service unit or by remote control from an external circuit positioned the skin surface, e.g. using a remote control.

For the system as described under any of FIGS. 1, 1A and 1B, a largely simplified surgery procedure can be applied in the method described below.

Making a first incision across the skin 101 and a portion of the fasciae 102;

Placing the second module 2 in a space between the musculus rectus abdominis fasciae 102, 102a. The second module 2 is preferably positioned on an antibiotic resorbable mat.

Making a second incision (e.g. across the skin 101) at a predefined location for forming a space for arranging subcutaneously the first module 1, which is also preferably placed on an antibiotic mat; and Making a tunnel between the first and second incisions for arranging the first tube 3 between the first module 1 and the second module 2. The tubing is coupled to the two modules.

The second module 2 (which locates at a deeper position than the first module 1) needs a less severe surgery than known systems because of the smaller size of the housing and a shape which is much better aligned with the local anatomy.

In this way, the first module 1 is fixated and ligated on the frontal rectus fascia 102 and the second module 2 is fixated between the frontal 102 and distal rectus fascia 102a. The abdominal wall is a multi-layer structure, including the fasciae 102a, 102b. These layers in the abdominal wall ensure the fixation of the system. Thus, dislocation of the system (especially the second module 2) at the early stage after implantation is largely reduced. As a result, the patient's comfort is improved and the hospital stay after the implantation reduced.

The shapes of first module 1 and the second module 2 may also be adapted for placing subcutaneously or intramuscularly in the abdominal wall, respectively. An embodiment is to be described below under FIG. 2.

Figure 2:
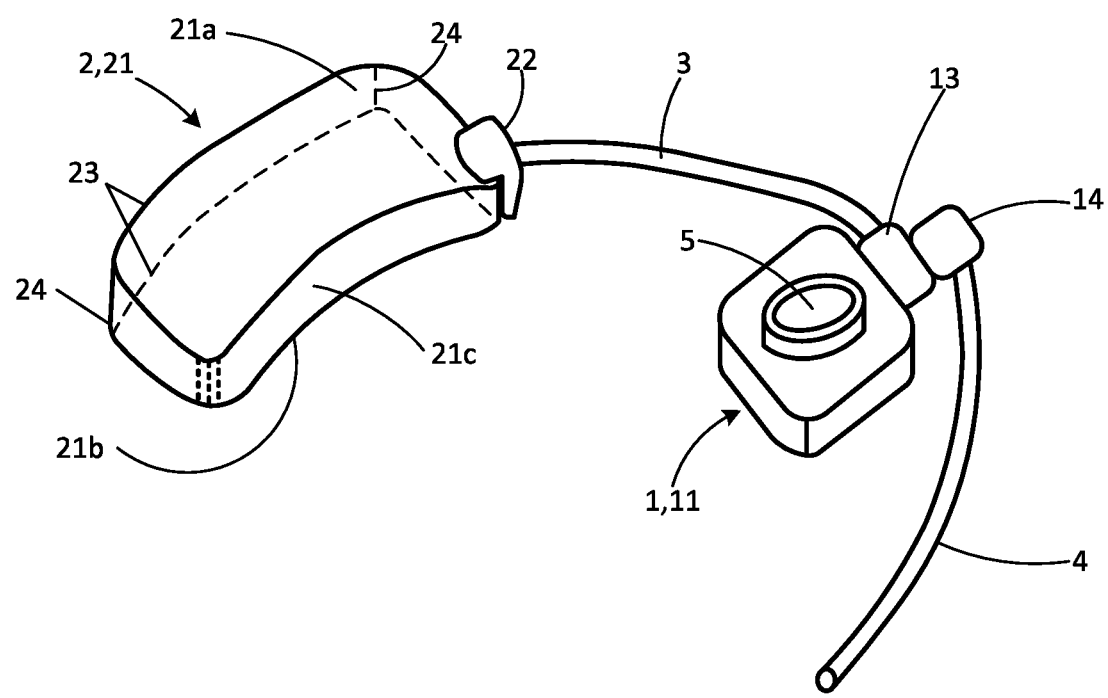
FIG. 2 shows a perspective view of an embodiment of the system of the invention.

FIG. 2 shows an embodiment of the system of the invention, which may comprise one or more elements as discussed above under FIG. 1. The First module 1 is arranged in a first housing 11, and the second module 2 is arranged in a second housing 21.

The first housing and the second housing are separated from each other and are connected via the first tube 3. The first housing 11 has a shape adapted to be arranged under the skin and one or more fat layers, and above the upper fascia 102 of the musculus rectus abdominis. The second housing 21 preferably has a shape adapted to be arranged between the musculus rectus abdominis fasciae. For example, the first housing 11 and the second housing 21 may comprise one or more rounded corners as shown in FIG. 2.

The first tube 3 and the catheter 4 may be provided with one or more connectors for mounting on the first housing 11. The one or more connectors make it easier to replace the first tube 3 or the catheter 4. In the embodiment shown, a first connector 13 is connected to the first tube 3, and a second connector 14 is connected to the catheter 4. In this way, the first tube 3 and the catheter 4 can be replaced independent of each other.

Further the system can be adapted prior to implantation to the size of the living body, e.g. using a first tube 3 of suitable length. The tube 3 connects the first module 1 and the second module 2. In the embodiment shown, the tube 3 is connected to a third connector 22, which is arranged to mount on the second module 2.

The catheter 4 has a length for extending through the Peritoneum into the abdominal cavity. Via the first tube 3, the medical substance or rinsing fluid can be conducted in both directions according to the setting of the multidirectional valves at the different units.

As shown in FIG. 2, the first module 1 may have an oval shape adapted to location under the skin 101, and the connector 13 that may be arranged at a side of the First module.

The second module 2 preferably has a shape adapted to the anatomy of the musculus rectus abdominis. The sum of the volumes of both volumes is hence smaller than a conventional implantable infusion pump as a single unit.

As shown in FIG. 2, the housing 21 of the second module 2 may comprise a first face 21a and a second face 21b facing each other. A face is a surface area defined by one or more edges. The first face 21a may edge the second face 21b. Alternatively, as shown in FIG. 2, the housing 21 may further comprise one or more side faces 21c, edging the first face 21a and the second face 21b. The first face 21a and the second face 21b are such that the housing 21 lacks a rotational symmetry/cylindrical symmetry. For example, in the embodiment shown, the first face 21a and the second face 21b both have bent/curved polygonal shapes, provided with one or more rounded corners.

The absence of cylindrical symmetry prevents rotation of the housing 21 in the abdominal wall after implantation.

Each of the polygonal shapes of the first face 21a and the second face 21b preferably comprise more than three and less than seven corners. If the number of the corners are too few (e.g. triangle), the corner might be too sharp (even with a rounded corner) and might make the patient itch. If the number of the corners are too many (e.g. seven or more), the polygon will look like a circle or ellipse, and has a higher possibility of rotation and/or slide.

The plate-like body of the second housing 21 preferably has a non-uniform thickness. For example, the first face 21a and the second face 21b preferably have a non-uniform distance. For example, the first face 21a and the second face 21b are preferably bent in the same direction with a different curvature, as shown in FIG. 2.

In this way, the non-uniform distance between the first face 21a and the second face 21b prevents the housing 21 from moving/displacing/dislocating in the abdominal wall. It can also minimize abrupt changes in thickness so the tissue can better form around it.

The embodiment of the second module 2 shown in FIG. 2 has all the above-mentioned advantages. The housing 21 having a plate-like shape having a general bar shape, preferably a wind shield shape. The first face 21a is a top face, and the second face 21b is a bottom face, and there are four side faces 21c. The top face and the bottom face are connected to the side faces 21c over two curved edges 23 having a length between 4-10 cm and over two generally straight edges 24 having a length between 0.5-4 cm. Preferably, the top face and/or the bottom face are curved in a direction substantially parallel to the straight edges thereof, and the top face and the bottom face preferably have a different curvature, as shown in FIG. 1 and FIG. 2.

The second module 2 in the shown embodiment has a shape similar to a "Salmon slice", having a plate-like structure, wherein the first face 21a and the second face 21b both have shapes of bended/curved rectangular, each having four rounded corners. The first face 21a and the second face 21b are bent in the same direction with different curvatures. As such, both rotation and dislocation of the housing 21 in the abdominal wall are avoided and the tissue can easily form around it.

In this way, hindrance experienced by patients in daily function and exercise (e.g. at sexual activities) are reduced. The anatomic friendly shape of the Second module 2 minimizes such hindrance and unpleasant feelings during all kind of activities.

Figure 3:
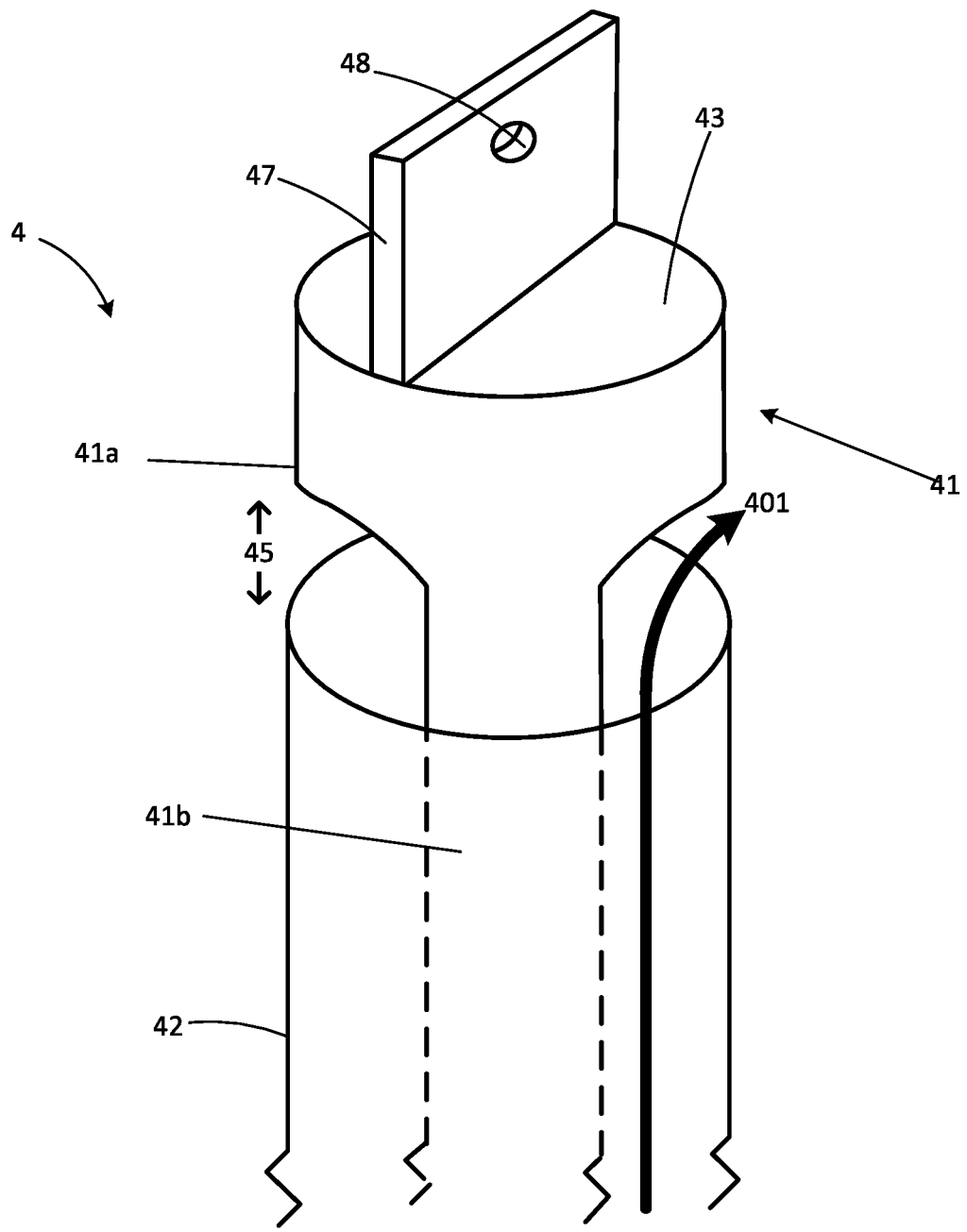
FIG. 3 shows a perspective view of an embodiment of a catheter for releasing medical substance according to the invention, the catheter comprising an outer tube and an inner core.

FIG. 3 shows an embodiment of the tip of catheter 4 of the insulin infusion system, which may comprise one or more elements as described above under FIG. 1 or 2. The catheter 4 comprises an inner core 41 and an outer tube 42. The inner core 41 and the outer tube 42 define a slit around a distal end of the outer tube 42 for releasing the medical substance, as shown in the arrow 401.

The system is arranged to make a relative movement 45 between the outer tube 42 and the inner tube 41. The relative movement 45 may be in an axial, rotational direction or a combination of the two. The first module 1 (e.g. the second connector 14 of the catheter) may comprise an electrical circuit for moving the inner core 41 and/or the outer tube 42. The system may also be arranged to adjust the location and/or orientation of the first module 1 and/or the second module 2, so that the relative movement 45 is induced. The relative movement is such that it disturbs a formation of a protein layer around the distal end of the catheter 4. The movement can be induced at one or more scheduled intervals, preferably separated by at least one hour (e.g. once or 2-3 times per day), and/or be induced in response to a control signal. The control signal may be generated on the basis of a parameter related to the formation of the protein layer, such as time.

Such a relative movement between the inner core 41 and the outer tube 42 has an advantage to disturb the formation of a protein sealing layer. Such a protein layer, caused by deposition of proteins at the tip of catheters, is undesired because this interferes or even may block the flow of insulin or other fluid. As the inner core 41 and the outer tube 42 have the relative movement from time to time, the formation of the protein layer is disturbed and can no longer hinder the release of the medical substance. It can also restrict crystalization on solutes of the medical substance such as insulin.

In the embodiment shown, the inner core 41 forms a closed flexible rod. As shown by the arrow 401, the medical substance flows through a space between the flexible rod and the outer tube 42. In one embodiment, the medical substance flows through this space all the way from the proximal end of the catheter 4 to the distal end of the catheter 4.

The embodiments using a closed flexible rod have an advantage that the relative movement is not only around the tip of the catheter, but substantially along an entire path of the flow of the medical substance. As the side wall of the inner core 41 and the inner side wall of the outer tube 42 also move relative to each other, the formation of the protein layer on the side walls can also be avoided. In this way, the formation of the protein layer can be avoided substantially along the entire path of the flow of the medical substance and also restrict crystalization.

The inner core 41 may comprise a first portion 41a having a larger radius at the distal end and a second portion 41b having a smaller radius. The radius of the first portion 41a preferably equals to the inner-radius of the outer tube so that the distal end of the catheter may have a lit like shape for closing the open distal end of the outer tube. The radius of the first portion 41a may also be slightly different from the inner-radius of the outer tube 42. The different radii of the first portion and the second portion can disturb a laminar flow of liquid around the distal end of the catheter. This can increase the effect of the relative movement to disturb the formation of the protein layer.

The catheter 4 may comprise a fixation element 47 for fixation in the living body. The fixation element 47 may be arranged on the inner core 41, preferably at the distal end 43 of the inner core. The distal end 43 preferably defines a generally flat surface, and the fixation element 47 preferably has a shape of a tongue extending substantially perpendicularly from the flat surface of the distal end 43 of the inner core. The tongue preferably has a generally cuboid shape. Preferably, the fixation element 47 comprises a hole 48 extending through the fixation element 47. In this way the distal end 43 of the catheter can be sutured and fixed in the living body.

Figure 4:
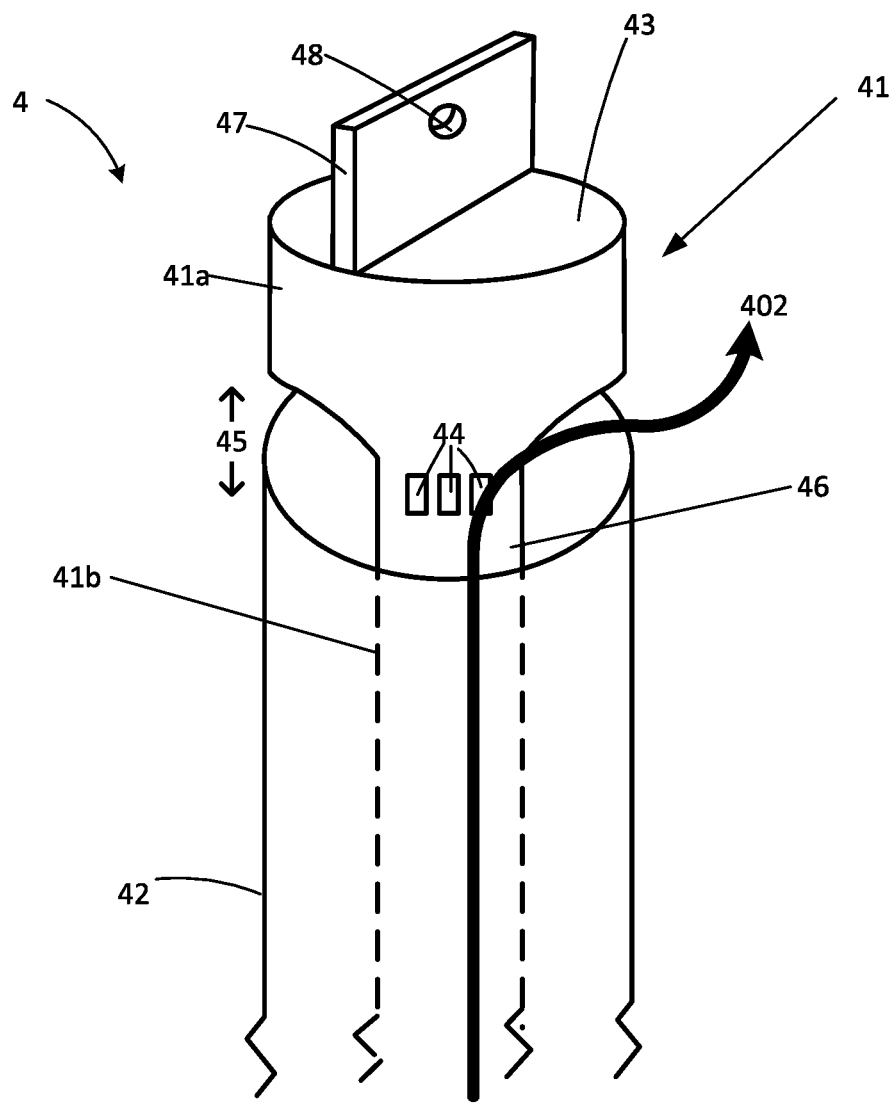
FIG. 4 shows another embodiment of a catheter of the invention, wherein the inner core has a form of a tube having a closed-end.

FIG. 4 shows another embodiment of the tip of catheter 4 of the insulin infusion system, which may comprise one or more elements as described above under FIG. 1, 2 or 3.

In this embodiment, the inner core 41 has a form of a tube having a closed-distal end 43 and a sidewall 46. The inner core 41 may comprise one or more openings 44 for releasing insulin, e.g. arranged on the side wall 46. As shown by the arrow 402, the medical substance first flows in the inner core, then flows into the openings 44. The inner core 41 and the outer tube 42 define a slit around a distal end of the outer tube 42 for releasing the medical substance via the openings 44, as shown in the arrow 402. The openings 44 are preferably arranged close to the slit.

Figure 5:
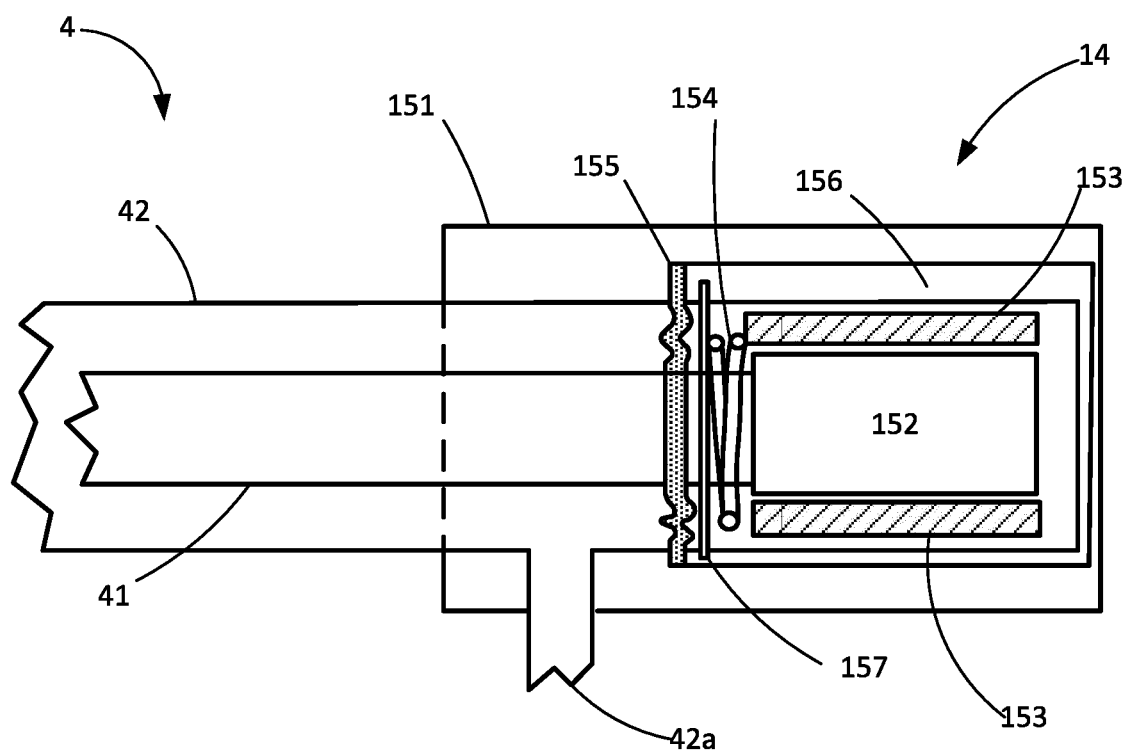
FIG. 5 shows an embodiment of a mechanism for performing the relative movement between the inner core 41 and the outer tube 42 of the catheter 4.

FIG. 5 shows an embodiment of a mechanism for performing the relative movement between the inner core 41 and the outer tube 42 of the catheter 4. In the embodiment shown, the mechanism is arranged in the second connector 14.

A proximal end of the outer tube 42 is connected to a cap 152. The cap 152 preferably comprises metal, preferably comprises a ferromagnetic material (e.g. iron). The cap 152 interacts with one or more inductive coils 153 (e.g. one or more solenoids) to relatively move the inner core 41 with respect to the outer tube 42.

The second connector 14 may comprise a spring 154 for asserting a restoring force on the cap 152. An end of the spring 154 may be fixed on a ring 157 for moving the cap 152. The ring 157 preferably comprises metal. The inductive coil 153 may be arranged to assert a force on the cap 152 in a direction substantially parallel to the restoring force of the spring 154. Alternatively or additionally, the inductive coil 153 may be arranged to relatively rotate the inner core 41 with respect to the outer tube 42.

The second connector 14 may comprise a housing 151 for accommodating the proximal end of the outer tube 42 and any other element described above. The housing 151 may be provided with a seal 155 (e.g. diaphragm) for defining a space 156 for accommodating electromagnetic/electronic circuit(s), wherein the seal 155 is arranged to restrict liquid from entering the space 156.

The outer tube 42 may comprise an inlet portion 42a for receiving the medical substance from the system, so that the medical substance can flow to the distal end of the catheter 4 in the space between the inner core 41 and the outer tube 42.

Figure 6:
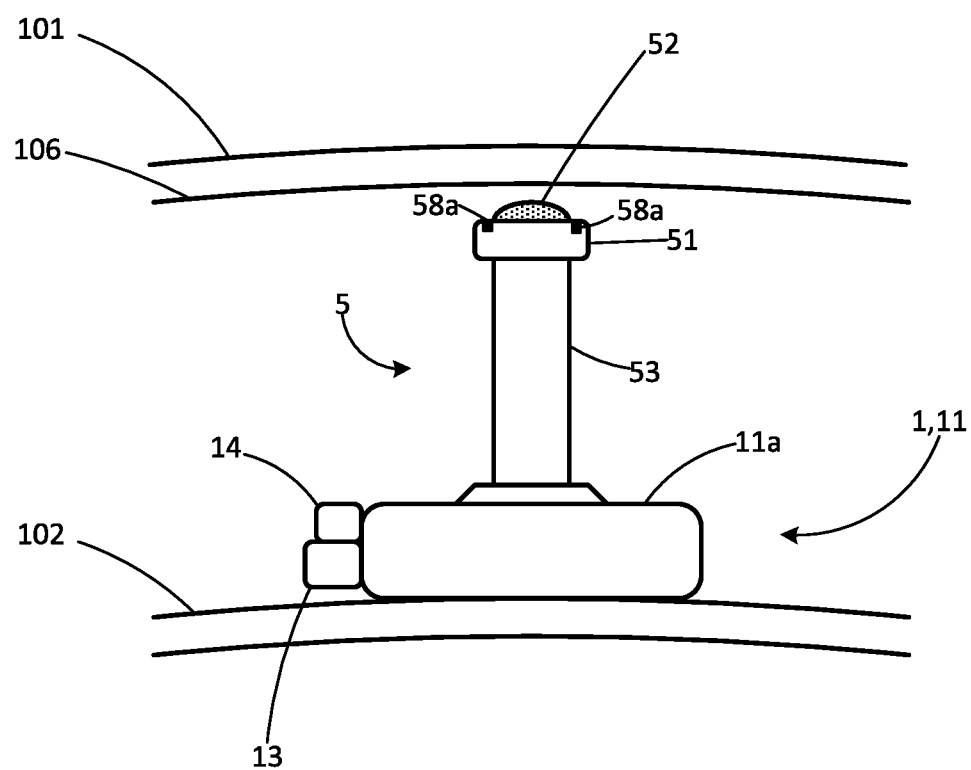
FIG. 6 shows a module for receiving medical substance according to the invention. The module has an inlet port adapted to the thickness of one or more subcutaneous fat layers. The length of the tunnel can be personalized as to fit the individual thickness of the one or more fat layers.

FIG. 6 shows an embodiment of the first module 1, which may comprise one or more elements as described above under FIGS. 1, 1A, 1B, 2-5, wherein the length of the inlet port 5 is adapted to the thickness of one or more fat layers between the skin 101 and a top layer of fascia 102.

In the embodiment shown, the inlet port 5 comprises an inlet 51 and an extending portion 53, which is adapted to extend from the first housing 11 substantially through all or most fat layers 106.

In this way, regardless of whether the patient is fat or thin, the inlet 51 can be arranged just under the skin. This can simplify processes of one or more of refilling, rinsing and charging, as it makes it easier to locate the inlet 51. For example, the charging circuit 55 as discussed above under FIG. 1A can have a location close to the skin 101.

Referring back to FIG. 6, the extending portion 53 may be selected from a plurality of adapters, each having a different pre-determined length and adapted to mount to the inlet 51 at one end and to the first housing 11 at the other end. For example, a kit of parts of the system can be provided for sale, wherein the kit comprises two or more such adapters. In another embodiment, the extending portion 53 may be mounted together with the inlet 51. A kit of parts or modules may comprise a plurality of inlets 51, each mounted with an extending portion 53 with different lengths. In yet another embodiment, the entire first module may form an integral unit, e.g. the first housing comprises a plate-like body, and an extending portion 53 forming a part of the same housing, extending or towering from a top surface 11a of the housing 11. The top surface 11a can be generally flat. plate-like body.

A plurality of interchangeable modules of the first housing may be provided in the kit, wherein each module of the first housing has a different length of the extending portion 53. The doctor may thus choose between different modules of the first housing with different lengths of the inlet port.

In this way, when implanting the system into the living body, one adapter with a suitable length may be selected among the plurality of adapters. The system after the implantation can therefore have an inlet port 5 which has a suitable length, extending from the first housing to a location just under the skin.

In one embodiment, the inlet 51 is provided with a sealing member 52 (e.g. comprising rubber or a similar material), for allowing puncturing by a needle or similar structure to refill/rinse the system.

The embodiments as described above have an advantage that the refilling procedure can be carried out at the close proximity to the skin. In this way, refilling can be considerably less time consuming. The cost and burden of the patient can thus be reduced.

The inlet port 5 may be integrated with an outlet function as an integrated inlet-outlet port. In the embodiment shown, the first module 1 is arranged in a first housing 11.

The first module may comprise a separate outlet port for discharging unused medical substance to outside the living body. The integrated inlet and outlet port may further be arranged to receive and discharge rinsing liquid for rinsing/cleaning the system and therefore connects to the first tube as well.

The descriptions above are intended to be illustrative, not limiting. It will be apparent to the person skilled in the art that alternative and equivalent embodiments of the invention can be conceived and reduced to practice, without departing from the scope of the invention, which is defined by the claims as set out below.

The invention claimed is:

1. A system adapted to be implanted in a living body for supplying medical substance, the system comprising:
   a first module having an inlet port for receiving a transcutaneous injection of the medical substance;
   a second module having a reservoir for storing the medical substance;
   a first tube, arranged to allow the medical substance to flow between the first module and the second module;
   an electrically powered pump; and
   a catheter for releasing the stored medical substance into the living body,
   wherein the first tube is arranged to allow the first module and second module to be implanted at different locations in the living body,
   wherein the catheter is connected to the first module,
   wherein the first module comprises an electrically controlled valve connected to the inlet port, to the first tube and to the catheter, the valve having three modes of operation,
   wherein in a first mode the valve connects the first tube to the catheter for supplying medical substance from the reservoir to the catheter,
   wherein in a second mode the valve connects the inlet port to the first tube for filling the reservoir and
   wherein in a third mode the valve directly connects the inlet port to the catheter for rinsing the catheter or to enable use of an external pump.

2. The system of claim 1, wherein the first tube is arranged to conduct the medical substance from and to the first module and the second module.

3. The system of claim 1, wherein the first module, is provided with a power supply for supplying an electronic power to the system.

4. The system of claim 1, wherein the first module, is provided with a rechargeable battery, and a charging circuit for receiving a contactless charging signal from a charging device, wherein the charging circuit is provided in or close to the inlet port.

5. The system of claim 4, the system further comprising a charging device for emitting a charging signal for the charging circuit.

6. The system of claim 1, wherein the first tube provides an electrical connection between the first module to the second module.

7. The system of claim 6, wherein the second module comprises the electrically powered pump for pumping the medical substance from and/or to the reservoir.

8. The system of claim 1, further comprising a glucose sensor for measuring a value representing a level of blood sugar, wherein the system is arranged to control release of the medical substance via the catheter in response to the measured value.

9. The system of claim 1, wherein a second housing of the second module has a closed-off an internal volume that receives the reservoir and wherein the reservoir is arranged to change a shape in dependence of an accumulated release of the medical substance, wherein the internal volume further is filled with a material adapted to transform between a liquid phase and a gas phase in in dependence of the internal volume.

10. The system of claim 1, wherein the first module is arranged in a first housing, wherein the inlet port comprises a self-sealing material.

11. The system of claim 10, wherein the inlet port is one or more of:
dome-shaped;
positioned on a generally flat side of the first housing;
shaped to extend from the first housing.

12. The system of claim 10, wherein the inlet port towers from the first housing in a range between 1 cm and 4 cm.

13. The system of claim 1, wherein the first module comprises a control circuit for controlling the second module to release the stored medical substance via the catheter.

14. The system of claim 1, wherein the first module is adapted to be positioned subcutaneous and the second module is adapted to be positioned deeper than the first module in the living body.

15. The system of claim 1, wherein the second module is arranged in a second housing, wherein the first tube has a length between 4 cm and 15 cm.

16. The system of claim 1, wherein the first module is arranged in a first housing, the second module is arranged in a second housing, and at least one of the first housing and second housing have a plate-like shape.

17. The system of claim 1, the second housing having a plate-like shape having a general bar shape having a top face and a bottom face and four side faces, wherein the top face and the bottom face are connected to the side faces over two curved edges and over two generally straight edges, wherein the top face and/or the bottom face are curved in a direction perpendicular to the straight edges thereof, the top face and the bottom face having a different curvature.

18. The system of any of claim 1, wherein the first module comprises a magnet or an electromagnetic coil, preferably in or close to the inlet port, to be attracted by an electromagnetic force generated outside the living human body.

19. The system of claim 18, further comprising a locator device for locating the first module by an electromagnetic force.

20. A system adapted to be implanted in a living body for supplying medical substance, the system comprising:
an inlet port for receiving a transcutaneous injection of the medical substance;
an electrically powered pump;
a housing, comprising a reservoir for storing the medical substance; and
a catheter for releasing the stored medical substance into the living body,
wherein the housing has a shape lacking a cylindrical symmetry, and
wherein the system further comprises an electrically controlled valve that is fluidly connected to the inlet port, to the reservoir and to the catheter, the valve having three modes of operation,
wherein in a first mode the valve connects the first tube to the catheter for supplying medical substance from the reservoir to the catheter,
wherein in a second mode the valve connects the inlet port to the first tube for filling the reservoir and
wherein in a third mode the valve connects the inlet port to the catheter for rinsing the catheter or to enable use of an external pump.

21. A kit of modules, for forming a system adapted to be implanted in a living body for supplying medical substance, the kit comprising:
a plurality of modules for forming a first housing for receiving a transcutaneous injection of the medical substance and for releasing the medical substance into the body; and
a catheter, to be connected to the first housing, for releasing the stored medical substance into the living body,
wherein the plurality of modules comprise two or more interchangeable inlet modules for adapting a length of an extending portion of the first housing.

22. The kit of modules of claim 21, wherein the plurality of modules comprises a valve for controlling a liquid flow.

* * * * *